United States Patent [19]

Vogt et al.

[11] Patent Number: 5,046,272
[45] Date of Patent: Sep. 10, 1991

[54] FLUID-OPERATED STABILIZING APPARATUS AND METHOD

[75] Inventors: Robert E. Vogt; Robert D. McQuiggin; Kenneth R. Schmidt, all of Neenah, Wis.; Jark C. Lau, Roswell, Ga.

[73] Assignee: Kimberly-Clark Corporation, Neenah, Wis.

[21] Appl. No.: 514,291

[22] Filed: May 1, 1990

[51] Int. Cl.⁵ .......................... D06C 3/00; D06F 67/04
[52] U.S. Cl. ........................................... 38/143; 26/87; 26/88; 38/8; 38/1 R
[58] Field of Search ..................... 38/1 R, 7, 8, 14, 64, 38/70, 143; 112/304, 306, DIG. 2; 69/19, 32, 33, 41; 223/37, 52; 271/6, 12, 13, 84, 195, 226; 414/13; 26/68, 87, 88, 98

[56] References Cited

U.S. PATENT DOCUMENTS

| | | | |
|---|---|---|---|
| 1,912,466 | 6/1933 | Remington | 38/8 |
| 1,912,724 | 6/1933 | Remington | 26/87 X |
| 1,997,267 | 4/1935 | Remington | 38/143 X |
| 2,635,370 | 4/1953 | Mann et al. | 38/143 |
| 3,464,131 | 9/1969 | McCabe | 38/143 |
| 3,553,863 | 1/1971 | Sjostrom | 414/13 X |
| 3,568,341 | 3/1971 | Buss | 38/143 |
| 3,874,043 | 4/1975 | Holm | 38/143 X |
| 4,053,967 | 10/1977 | Mair | 38/143 X |
| 4,197,621 | 4/1980 | Mair | 38/143 X |
| 4,516,760 | 5/1985 | Stumf | 26/87 X |
| 4,702,468 | 10/1987 | Pollich | 271/195 |
| 4,750,442 | 6/1988 | Keeton | 112/304 X |
| 4,885,853 | 12/1989 | McCabe | 38/8 X |

Primary Examiner—Werner H. Schroeder
Assistant Examiner—Ismael Izaguirre
Attorney, Agent, or Firm—Douglas L. Miller

[57] ABSTRACT

A fluid-operated stabilizing apparatus receives an article having loose, wrinkled overlapping surfaces and by use of fluid flow control devices directs flows of fluid to the overlapping surfaces to fluidly shake the surfaces to smooth out wrinkles and any folded portions thereof, and then to align and hold the surfaces for subsequent treatment, such as bonding together. A method is also provided for smoothing and aligning the overlapping surfaces for subsequent treatment.

38 Claims, 5 Drawing Sheets

FLUID-OPERATED STABILIZING APPARATUS AND METHOD

BACKGROUND OF THE INVENTION

This invention pertains to an apparatus and method for aligning the overlapping edge portions of an article, and more particularly to a fluid-operated stabilizing apparatus and method that utilizes a combination of fluid flows against overlapping and wrinkled edge portions to smooth them out and align them for subsequent treatment or handling.

Various types of disposable garments are currently available for use, such as baby diapers, child training pants, adult incontinence garments, and the like. In manufacturing these disposable garments, it is highly desirable that the speed or rate of manufacture of the garments be as high as possible in order to maximize the use of numerous manufacturing lines. During the manufacture of a particular garment, it may be desirable to align two different layers of material together for subsequent treatment, or to fold the garment upon itself and then align its folded or overlapping edge portions for subsequent treatment, such as bonding. As the speeds or rates of manufacture of the garments increase, certain problems may arise that need to be corrected in order to manufacture a quality garment acceptable to the consumer.

One of these problems during a process of folding a garment upon itself or placing two layers of material together is that some or all of the edges are wrinkled, folded-over, or unaligned, and therefore cannot be properly treated at a subsequent handling station.

A second problem is that the wrinkled state and unalignment of these edges is greatly exacerbated as the speed of manufacture is increased. This is generally caused by the increased rate of manipulation, placement of layers together, or folding of the garment, and the increased turbulence of the air flow against the layers or garment created by the increased speed.

SUMMARY OF THE INVENTION

In one form of the present invention, there is provided an assembly for fluidly handling a loose, wrinkled edge portion of an article comprising a conveying mechanism for conveying the article having the loose, wrinkled edge portion, and a fluid-extending mechanism for receiving the article and for fluidly extending the loose, wrinkled edge portion to substantially smooth-out the wrinkles therein. A fluid-holding mechanism fluidly holds the edge portion in its substantially smoothed-out state, and the conveying means then conveys away the article and its substantially smoothed-out edge portion.

In another form of the present invention, there is provided a method of handling an article having wrinkled, overlapping surfaces, comprising the steps of receiving the article having the wrinkled, overlapping surfaces, smoothing-out the overlapping surfaces, maintaining the surfaces in the smoothed-out condition, and then transporting the article with smoothed-out overlapping surfaces.

BRIEF DESCRIPTION OF THE DRAWINGS

The above-mentioned and other features and objects of this invention, and the manner of attaining them, will become more apparent and the invention itself will be better understood by reference to the following description of an embodiment of the invention taken in conjunction with the accompanying drawings wherein.

DESCRIPTION OF A PREFERRED EMBODIMENT

Figure 1:
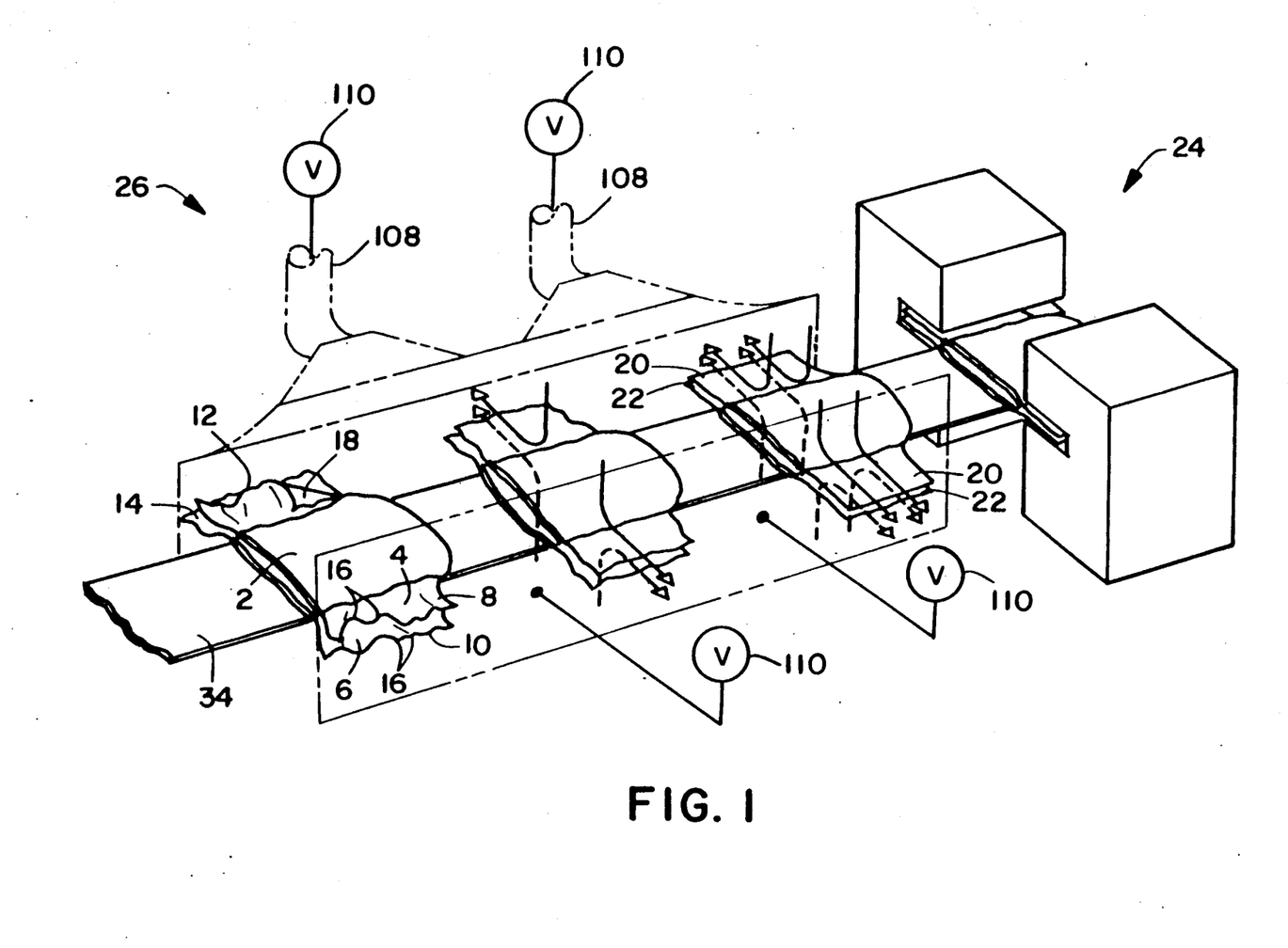
FIG. 1 is a perspective view partly in phantom illustrating the operation on a folded article by one embodiment of the present invention.

Referring to FIG. 1, there is illustrated article 2 in progressive stages as it proceeds through the present invention. Article 2 is illustrated as a pant-like garment folded in half transversely across the crotch area and having loose, wrinkled, unaligned edge portions or flaps 4, 6 in a generally overlapping relationship. The uppermost pair of flaps 4 have outwardly facing sides or surfaces 8 and ends 12, and the lowermost pair of flaps 6 have outwardly facing sides or surfaces 10 and ends 14. As illustrated, article 2 has been folded upon itself and flaps 4, 6 have a plurality of wrinkles 16 and a folded-over section 18 resulting from the folding. The term "folded-over" also includes similar terms such as "folded-under", "folded upon itself", and the like.

The present invention is operable on other types of article designs other than the folded-over pant-like article illustrated. Article 2 may be a folded diaper, child training pant, adult incontinence garment, and the like, or can be two sheets or layers of material overlappingly placed together for subsequent alignment and treatment. The use of the term "overlapping" or any variations thereof includes totally or partially superimposing one surface upon another. Partial overlapping is illustrated in FIG. 1 with the loose, aligned flaps 4, 6.

As article 2 travels through the present invention as illustrated in FIG. 1, loose, wrinkled, unaligned flaps 4, 6 are being progressively stabilized by the invention which results in smoothed-out or straightened flaps 20, 22 that are subsequently conveyed to handling station 24 for treatment, such as bonding together. The term "stabilizing" or any variations thereof includes the smoothing-out or straightening, holding, and then aligning of flap ends 12, 14. The present invention can align flaps 4, 6 so that they are coextensive at their ends 12, 14, or have an off-set alignment such that one end may extend beyond the other end a predetermined distance. Generally, whether edge portions or flaps 4, 6 will be ultimately aligned coextensively or off-set will be determined by the initial folding or handling step for garments or the initial superposing step of sheets or layers of material.

Figure 2:
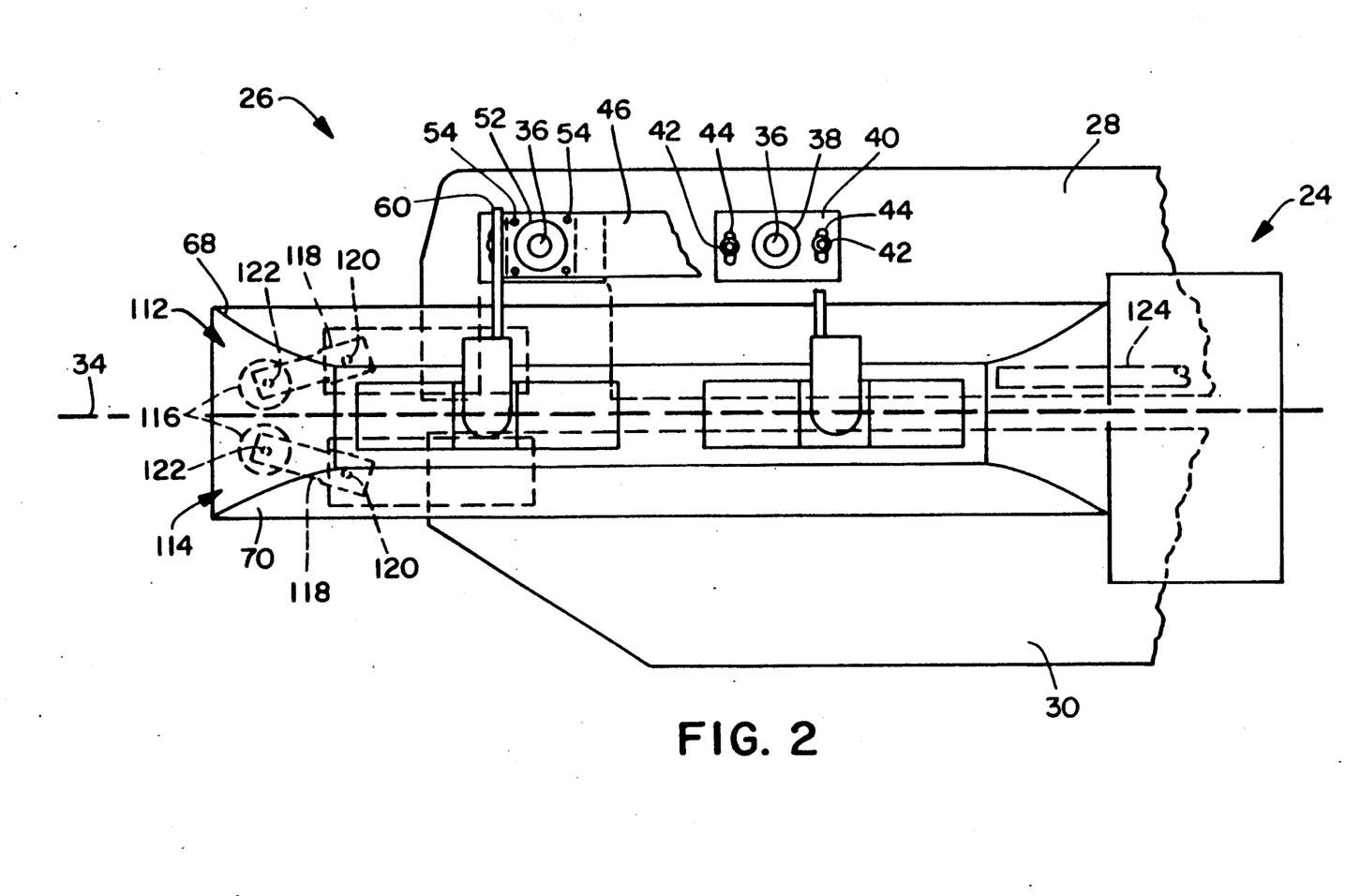
FIG. 2 is a fragmentary side elevational view partly broken away illustrating the embodiment of the invention in FIG. 1.
Figure 3:
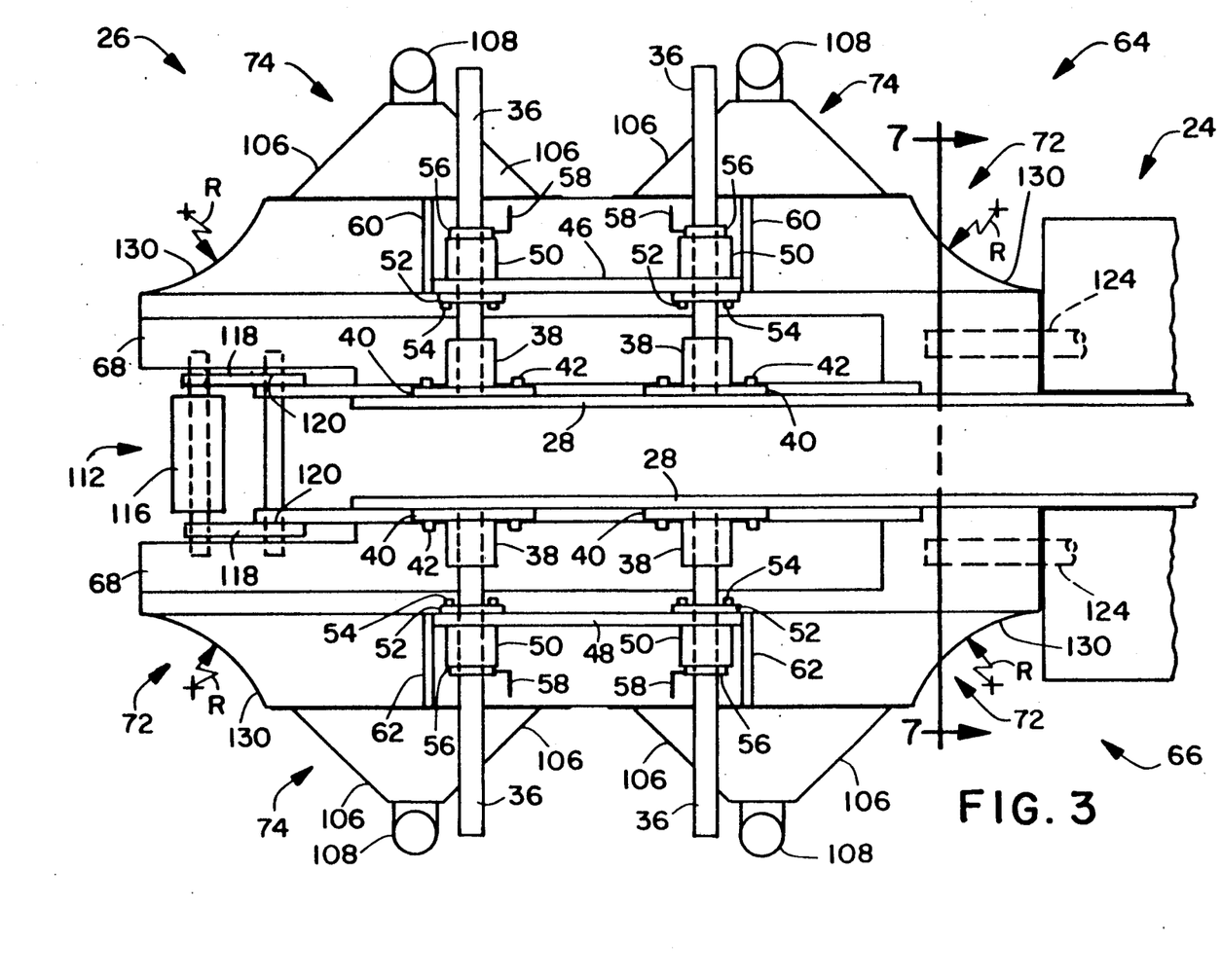
FIG. 3 is a fragmentary top plan view of the invention in FIG. 2.
Figure 4:
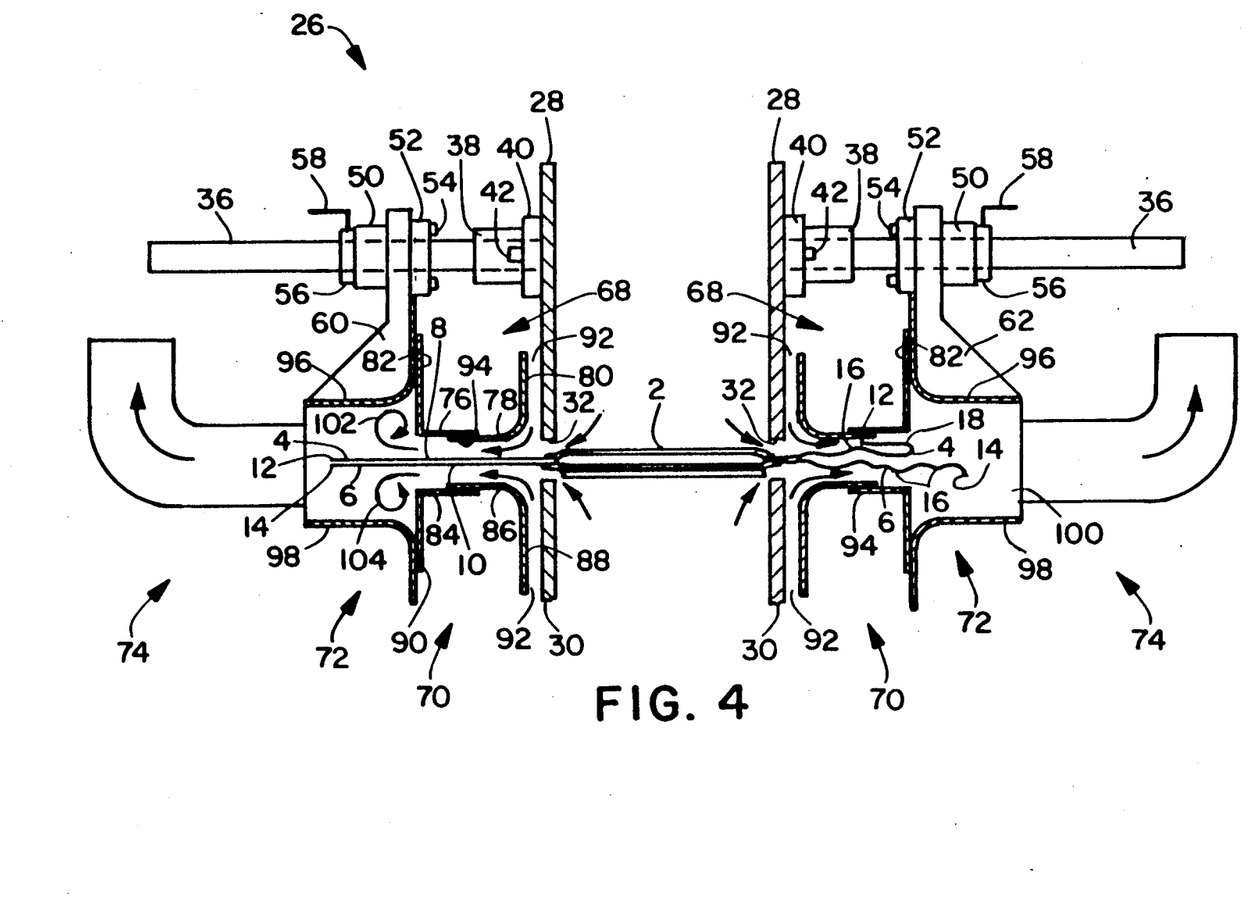
FIG. 4 is a fragmentary end sectional view of the invention in FIG. 3.

Referring to FIGS. 2, 3, and 4, fluid-operated stabilization system 26 of the present invention is illustrated in a preferred embodiment. Although the term "fluid" means "air" in this particular embodiment of the present invention, it also includes any gaseous medium and, if the article so requires, any liquid medium. A pair of vertically disposed and spaced-apart upper frame members 28 and a pair of vertically disposed and spaced-apart lower frame members 30 (FIG. 4) form between their mutually-facing ends a horizontally elongated passageway 32 (FIG. 4) through which article 2 is conveyed by continuous conveyor belt 34 (FIGS. 1 and 2). As illustrated in FIG. 3, four cylindrical support arms 36 are connected to upper frame members 28. Two of the support arms 36 are connected to one of the upper frame members 28 and the other two support arms 36 are connected to the opposite upper frame member 28, and all of the support arms 36 extend outwardly away from frame members 28. Each support arm 36 is connected to its respective upper frame member 28 by means of a bushing 38 and pillow block 40. In this embodiment, each set of a bushing 38 and pillow block 40 is integral, but each set can also be separate elements joined in any suitable manner. Pillow block 40 and bushing 38 are vertically adjustably secured to an upper frame member 28 by means of screws 42 received through oblong openings 44 (FIG. 2) in a respective upper frame member 28. As illustrated in FIG. 2, oblong openings 44 permit a pillow block 40, bushing 38, and support arm 36 to be vertically adjusted relative to conveyor belt 34.

Use of the terms "vertical", "vertically", "horizontal", and "horizontally" have their usual meaning in this embodiment of the present invention. However, the present invention contemplates that vertical surfaces can be "generally vertically" disposed if desired and would thus be oriented between the true vertical position and about a 45° position relative to the true vertical position. The same interpretation for "generally horizontally" disposed means an orientation between the true horizontal and about a 45° position relative thereto.

Referring to FIG. 3, support plate 46 is connected between a cooperating pair of support arms 36, and a similar support plate 48 is connected between the other cooperating pair of support arms 36. The connections of support plates 46, 48 are identical, so a description of only support plate 46 will be made with reference to FIGS. 2-3. Support plate 46 has a pair of openings for slidably receiving therethrough respective support arms 36. A pair of sleeve bearings 50 are slidably received on respective support arms 36 on one side of support plate 46, and a pair of clamps 52 are slidably received on respective support arms 36 on the opposite side of support plate 46. Sleeve bearings 50 and clamps 52 have openings therein for receiving support arms 36 therethrough, and a plurality of screws 54 are received through openings in clamps 52, support plate 46, and threadedly secured in threaded openings in sleeve bearings 50. Each set of a sleeve bearing 50 and clamp 52 is slidably, adjustably secured to a respective support arm 36 by a locking collar 56 releasably secured by a lever 58 to a support arm 36. Each lever 58 is threadedly received through a threaded opening in a respective locking collar 56 and can be screwed hard against a respective support arm 36 to lock each set of a sleeve bearing 50 and clamp 52. Thus, by loosening levers 58, one or both of the support plates 46, 48 can be horizontally adjusted along its respective pair of support arms 36, which moves support plates 46, 48 inwardly or outwardly relative to conveyor belt 34 and the article 2 being conveyed therealong.

Support plate 46 has a pair of horn brackets 60 that are connected to the opposite ends thereof and depend downwardly therefrom, and support plate 48 similarly has a pair of horn brackets 62 that are connected to the opposite ends thereof and depend downwardly therefrom. Horn brackets 60, 62 are joined to their respective support plates 46, 48 in any suitable manner, such as by welding, and are movable with their respective support plates 46, 48 along cooperating support arms 36.

Fluid handling assembly 64 (FIG. 3) is secured to horn brackets 60, and an oppositely disposed fluid handling assembly 66 is similarly secured to horn brackets 62. Fluid handling assemblies 64, 66 operate identically, so a description of fluid handling assembly 64 will only be made. Fluid handling assembly 64 generally comprises upper baffle 68, lower baffle 70, vacuum horn 72, and vacuum duct 74 (FIG. 4). Upper baffle 68 comprises upper outer wall 76 (FIG. 4), upper inner wall 78 slidably disposed with upper outer wall 76, upper vertical wall 80 that is integral with upper inner wall 78, and upper vertical partition 82 that is integral with upper outer wall 76. Similarly, lower baffle 70 comprises lower outer wall 84, lower inner wall 86 slidably disposed with lower outer wall 84, lower vertical wall 88 that is integral with lower inner wall 86, and lower vertical partition 90 that is integral with lower outer wall 84.

Continuing to refer primarily to FIG. 4, upper and lower vertical walls 80, 88 are spaced-apart from their respective upper and lower frame members 28, 30 to form a pair of vertically disposed and mutually-facing channels 92 for directing an inward flow of air, as indicated by the arrows. Inward flows of air are also directed between frame members 28, 30 through passageway 32, as indicated by the arrows.

Upper outer and inner walls 76, 78 are spaced from lower outer and inner walls 84, 86 to form therebetween a passage 94 that is in fluid communication with channels 92. FIG. 4 illustrates article 2 being conveyed through passageway 32 such that edge portions 4, 6 also pass through passages 94 and vacuum horns 72.

Baffles 68, 70 are adjustable with respect to each other such that passage 94 can be shortened or lengthened by slidably moving upper outer and inner walls 76, 78 with respect to each other and lower outer and inner walls 84, 86 with respect to each other. Similarly, baffles 68, 70 can be adjusted to increase or decrease the width or height of passage 94 by moving walls 76, 78 and walls 84, 86 toward or away from each other.

Vacuum horn 72 comprises an upper horn wall 96 and lower horn wall 98 forming therebetween chamber 100 that is in fluid communication with passage 94. Because the width or height of chamber 100 is greater than the width or height of passage 94, as the flow of fluid passes through passage 94 and into the larger void of chamber 100, vortices of turbulent air flow are created as indicated by the curved arrows in chamber 100. The turbulent air flows located within chamber 100 are upper vortex zone 102 and lower vortex zone 104, both of which extend horizontally along vacuum horn 72 in a direction generally parallel to conveyor belt 34. As illustrated in FIG. 4, upper vortex zone 102 is formed by upper horn wall 96 and upper vertical partition 82, and lower vortex zone 104 is formed by lower horn wall 98 and lower vertical partition 90. Both vortex zones 102, 104 are near the juncture of passage 94 and chamber 100.

Vacuum duct 74 is connected in fluid communication with vacuum horn 72 and has duct side walls 106 (FIG. 3) that converge from vacuum horn 72 to vacuum tube 108. As illustrated in FIG. 1, each vacuum tube 108 is operably connected to an air pump or vacuum source 110 that draws the fluid flows as indicated by the arrows in FIGS. 1 and 4.

Referring to FIGS. 2 and 3, conveyor belt 34 conveys an article 2 in a left-to-right direction as viewed in the figures. As article 2 is conveyed toward fluid stabilization system 26, upper and lower nip roll assemblies 112, 114 contact and slightly compress the central portion of article 2 between frame members 28, 30 (FIG. 4) to initially hold article 2 in place as fluid stabilization system 26 begins to stabilize loose, wrinkled, and unaligned flaps 4, 6. Nip roller assemblies 112, 114 each comprise a roller 116 freely mounted on axis 122 which in turn is mounted between a pair of pivot arms 118. Pivot arms 118 are pivotally connected at pivot points 120 and are biased inwardly against article 2. Pivot arms 118 can be spring or pneumatically (not shown) biased toward article 2.

Figure 7:
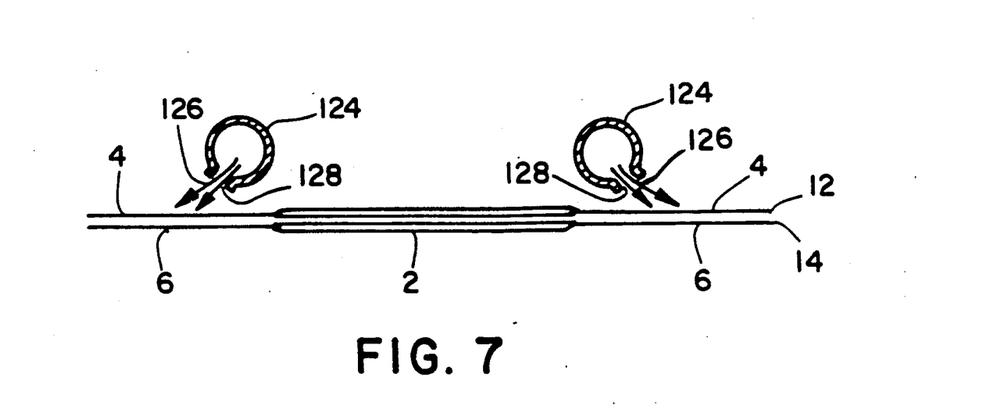
FIG. 7 is a fragmentary sectional view of FIG. 3 taken generally along line 7—7.

Referring to FIGS. 2, 3, and 7, a pair of elongate overhead ducts 124 are positioned above stabilized article 2 and each duct 124 comprises an elongate nozzle 126 with flared surfaces 128. As air flows through air ducts 124 and out elongate nozzles 126, the air flow impacts at an acute angle directed toward the ends 12, 14 to keep flaps 4, 6 in their smoothed, straightened alignment. Flared surfaces 128 serve to spread or scatter the air flow across a majority of the outer surfaces 8, 10 of flaps 4, 6. Although not illustrated, conveyor belt 34, other conveyor belts on each side and below pairs of flaps 4, 6, or fixed shelf members provide support underneath flaps 4, 6 against the air flows directed from ducts 124.

Referring to FIG. 3, each vacuum horn 72 has a curved surface 130 at its entrance and exit regions. Important to the proper and smooth operation of the present invention is the radius R of curved surface 130. Curved surfaces 130 gently and in an increasing and then in a decreasing manner, respectively, apply the effects of the fluid flow as it impinges flaps 4, 6. If the fluid flow effect is applied too abruptly, the loose, wrinkled, unaligned condition of flaps 4, 6 can be further exacerbated. Similarly, if the fluid flow effect is terminated too abruptly, the smoothed-out flaps 4, 6 may wrinkle or fold over. Thus, curved surfaces 130 very gently and smoothly apply and terminate the stabilizing effect of the fluid flow created by fluid stabilization system 26 of the present invention. The radius R is dependent upon several factors, such as the stiffness and weight of the article. A stiffer or heavier article requires a smaller radius R, as well as an increase in air flow velocity. Other factors upon which radius R is dependent include the velocity of article 2 as it is conveyed by conveyor belt 34 through fluid stabilization system 26 and the other fluid flow rates within system 26.

As an example, if article 2 is a small garment, such as a baby diaper or child training pant, radius R would generally be in the range of between about 1 centimeter (cm) to about 50 cm, and the fluid flow rates would generally be between about 3,000 to about 7,000 linear feet per minute with a static pressure within the range of about 2 inches to about 4 inches water below the ambient pressure.

Figure 5:
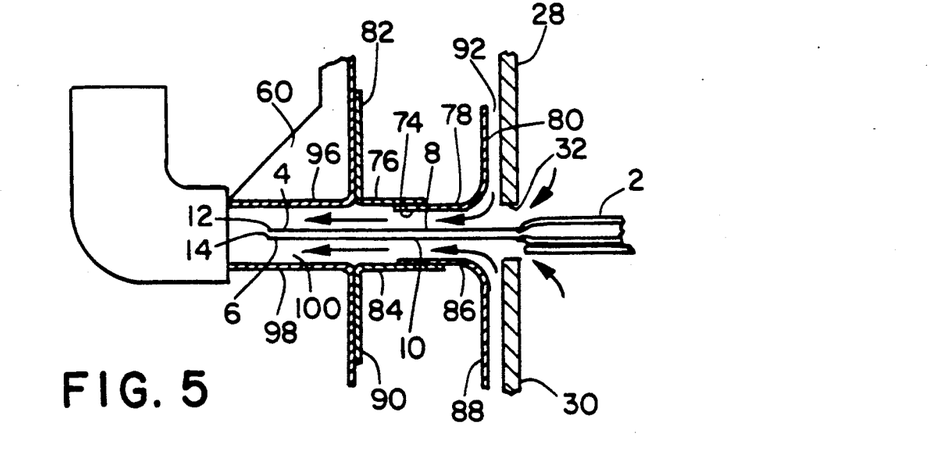
FIG. 5 is a fragmentary view similar to FIG. 4 of an alternate embodiment of the present invention.

Also unique to the present invention is the ability to vary the fluid effects of vortex zones 102, 104 and to move the zones 102, 104 within chamber 100. Referring to FIG. 5, the fluid effects of vortex zones 102, 104 can be varied between the turbulent effect illustrated in FIG. 4 and a substantially non-turbulent or laminar effect illustrated in FIG. 5. In FIG. 5, upper horn wall 96 and lower horn wall 98 have been moved inwardly to substantially parallel upper outer wall 76 and lower outer wall 84 such that passage 94 and chamber 100 have substantially the same width or height. An embodiment similar to that in FIG. 5 would be utilized when flaps 4, 6 are made of a very light, delicate woven or nonwoven web of material. By varying the heights or widths of passage 94 and chamber 100, the fluid effects of vortex zones 102, 104 can be varied as desired. As illustrated in FIG. 5, the effects of vortex zones 102, 104 have been effectively eliminated.

Figure 6:
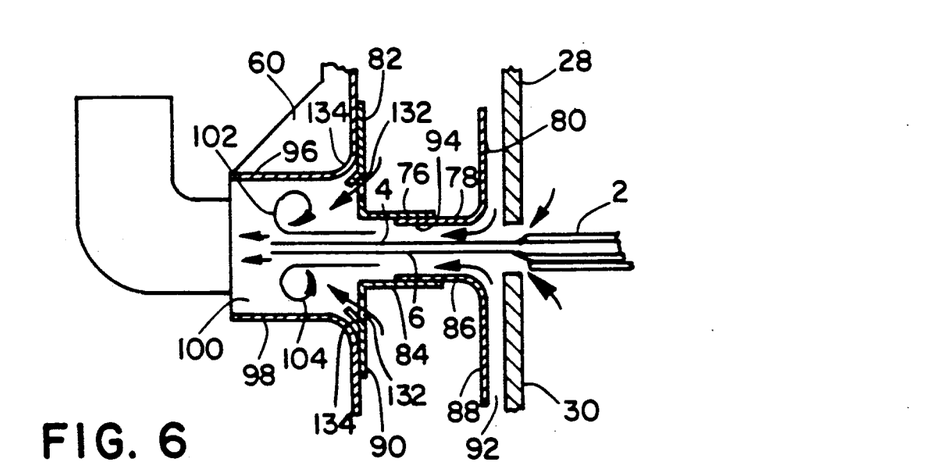
FIG. 6 is a fragmentary view similar to FIG. 4 of another alternate embodiment of the present invention.

The position, size, and strength of vortex zones 102, 104 within chamber 100 can also be adjusted as illustrated in FIG. 6. In FIG. 6, upper vertical partition 82 and lower vertical partition 90 have a plurality of openings 132 therein through which air can be drawn as illustrated by the arrows. If desired, slats 134 can be mounted on their respective partitions for directing the flow of air. Slats 134 can be fixed in position or hingedly mounted. With openings 132 in partitions 82, 90, vortex zones 102, 104 have been laterally moved to the left as illustrated in FIG. 6. Moving vortex zones 102, 104 further to the left in FIG. 6, which moves the zones 102, 104 closer to the ends 12, 14 of flaps 4, 6 may be necessary due to the stiffness or other material characteristics of flaps 4, 6. Although not illustrated in FIG. 6, directing the flow of air in a direction toward upper horn wall 96 and lower horn wall 98 vertically adjusts vortex zones 102, 104. Exactly at what point or position within chamber 100 that vortex zones 102, 104 should be located is dependent upon the length of flaps 4, 6, their material characteristics such as stiffness, drape, and the like.

Although the figures show two vacuum horns 72 and four vacuum ducts 74, a fewer number or greater number can be provided and is dependent upon the size, shape, and material characteristics of which article 2 is made.

Finally, the angle of impact or impingement of the fluid flows against article 2 through passageway 32, channels 92, passage 94, chamber 100, air ducts 124, and openings 132 would be dependent on the vacuum level and vary between 0° to about 90° relative to the horizontally disposed plane in which article 2 lies.

In operation, article 2 is conveyed by conveyor belt 34 (FIG. 1) to fluid stabilizer system 26 and between upper and lower nip roll assemblies 112, 114. Flaps 4, 6 of article 2 are loose, wrinkled, and unaligned as they approach nip roll assemblies 112, 114. As article 2 proceeds along its travel path defined by conveyor belt 34, curved surfaces 130 of vacuum horns 72 begin to gently apply the fluid effects on flaps 4, 6. In FIG. 4, the right-hand flaps 4, 6 are illustrated in their loose, wrinkled, and unaligned condition as they just enter vacuum horn 72. As the flows of air created by vacuum sources 110 flow in the direction of the arrows through passageway 32 and channels 92, the wrinkled surfaces 8, 10 begin to smooth or straighten out under the impact or impingement of the air flows. In order to fully extend flaps 4, 6, which may have a plurality of folded-over sections 18 (FIG. 1) or other unusually difficult wrinkles, turbulent air flow within vortex zones 102, 104 causes flaps 4, 6 to be fluttered or rapidly shaken. This causes any folded-over sections 18 and other unusually difficult wrinkles to be shook-out so that flaps 4, 6 can be smoothed or straightened, as illustrated by the left-hand flaps 4, 6 in FIG. 4. As smoothed-out article 2 approaches curved surfaces 130 on the right-hand side of FIG. 3, surfaces 130 begin to gently and smoothly terminate the effect of the fluid flow to maintain flaps 4, 6 in their smooth condition.

After flaps 4, 6 have been smoothed-out or straightened-out as illustrated in FIG. 4, they are maintained in that smooth condition as they proceed to handling station 24 by the fluid flow effects created by air ducts 124 in FIG. 7. The outwardly directed flow through flared surfaces 128 of nozzles 126 prevents any new wrinkles and maintains the coextensive alignment of ends 12, 14. Although FIG. 7 illustrates ends 12, 14 as being coextensive, the present invention can also align ends 12, 14 in an off-set manner. Handling station 24 then receives the smoothed and aligned article 2 for further treatment, such as bonding ends 12, 14 together by an adhesive material, heat sealing, ultrasonic bonding, or the like.

While this invention has been described as having a preferred embodiment, it will be understood that it is capable of further modifications. This application is therefore intended to cover any variations, uses, or adaptations of the invention following the general principles thereof, and including such departures from the present disclosure as come within known or customary practice in the art to which this invention pertains and fall within the limits of the appended claims.

What is claimed is:

1. A fluid-operated stabilizing system comprising:
   a fluid handling assembly comprising an entrance region and an exit region,
   a conveyor means extending at least between said entrance region and said exit region and defining therebetween a generally horizontally disposed travel path, whereby said conveyor means conveys along said travel path an article having wrinkled overlapping surfaces,
   said fluid handling assembly further comprising a generally vertically disposed fluid channel along one edge portion of and spaced apart from said generally horizontally disposed travel path, whereby a fluid flow is directed through said fluid channel onto the wrinkled overlapping surfaces of the conveyed article to substantially smooth-out the wrinkles,
   said fluid handling assembly further comprising a generally horizontally disposed fluid conduit in fluid communication with said fluid channel, whereby at least a portion of the overlapping surfaces is received therein and the fluid flow is directed through said fluid conduit and along the overlapping surfaces to further substantially smooth-out the wrinkles and to maintain the overlapping surfaces in a smoothed-out condition while the article is conveyed to said exit region, and
   a vortex-generating means in said fluid conduit for varying turbulence in a fluid zone therein, whereby the overlapping surfaces are fluttered or rapidly shaken to assist in the smoothing out thereof.

2. The system of claim 1 wherein said fluid conduit comprises a fluid passage in fluid communication with said fluid channel and a fluid chamberway in fluid communication with said fluid passage, said fluid chamberway having a height greater than a height of said fluid passage, said fluid zone being near a juncture of said fluid passage and said fluid chamberway.

3. The system of claim 1 wherein said fluid zone is movable within said fluid conduit.

4. The system of claim 1 wherein said vortex-generating means varies the position of said fluid zone within said fluid conduit.

5. The system of claim 1 wherein said vortex-generating means varies the size of said turbulent fluid zone within said fluid conduit.

6. The system of claim 1 wherein said fluid channel is generally vertically disposed between 0° to about 90° to said horizontally disposed travel path.

7. The system of claim 1 wherein said generally vertically disposed fluid channel is variable in width.

8. The system of claim 1 wherein said fluid channel is generally vertically and generally horizontally movable with respect to said travel path.

9. The system of claim 1 wherein said generally horizontally disposed fluid conduit is variable in height.

10. The system of claim 1 wherein said generally horizontally disposed fluid conduit is variable in length.

11. The system of claim 1 wherein said fluid conduit is generally vertically and generally horizontally movable with respect to said travel path.

12. The system of claim 1 wherein said fluid handling assembly further comprises a generally convexly curved surface at said entrance region, whereby the fluid flow is gently and in an increasing manner applied to the wrinkled overlapping surfaces.

13. The system of claim 1 wherein said fluid handling assembly further comprises a generally convexly curved surface at said exit region, whereby the fluid flow is gently and in a decreasing manner terminated over the smoothed-out overlapping surfaces.

14. The system of claim 12 or 13 wherein said curved surfaces have a radius of curvature between about 1 cm to about 40 cm.

15. The system of claim 1 further comprising a generally horizontally disposed fluid duct near said exit region and spaced apart from said one edge portion of said generally horizontally disposed travel path, whereby a fluid flow is directed on said overlapping surfaces to maintain said overlapping surfaces in said smoothed-out condition.

16. An article handling apparatus comprising:
   a work station including a generally horizontally disposed travel path, whereby said work station receives at least partially overlapping surfaces continuously moving along said generally horizontally disposed travel path and having respective loose, wrinkled edge portions that are unaligned relative to each other,
   fluid-straightening means along at least a portion of said generally horizontally disposed travel path for directing a flow of fluid therealong, whereby said fluid straightening means straightens the wrinkled edge portions,
   a fluid-aligning means comprising a pair of generally horizontally disposed fluid intake ducts, one of said fluid intake ducts being along one edge portion of the generally horizontally disposed travel path and the other of said fluid intake ducts being along an opposite edge portion of the generally horizontally disposed travel path, whereby generally horizontally directed flows of fluid through said fluid intake ducts are directed along respective ones of the loose, wrinkled edge portions to substantially align them together, and holding means along at least a portion of said generally horizontally disposed travel path for directing a flow of fluid therealong, whereby said holding means holds the substantially aligned edge portions together.

17. The apparatus of claim 16 wherein said fluid-straightening means comprises a pair of generally vertically disposed fluid exhaust ducts, one of said fluid exhaust ducts being along one side of the generally horizontally disposed travel path and the other of said fluid exhaust ducts being along an opposite side of the generally horizontally disposed travel path, whereby generally vertically directed flows of fluid through said fluid exhaust ducts are impinged on respective ones of the loose, wrinkled edge portions to straighten-out the wrinkles therein.

18. The apparatus of claim 16 wherein said fluid-aligning means substantially coextensively aligns the edge portions together.

19. The apparatus of claim 16 wherein said fluid-aligning means aligns the edge portions with a predetermined off-set.

20. The apparatus of claim 16 wherein said fluid-straightening means and said fluid-aligning means are movable relative to said travel path, thereby accommodating overlapping surfaces of different sizes.

21. The apparatus of claim 16 wherein said holding means is a pair of generally horizontally disposed fluid duct members.

22. A fluid operated assembly, comprising
conveying means for conveying an article having a loose, wrinkled edge portion, fluid-extending means for fluidly extending the loose, wrinkled edge portion to substantially smooth-out the wrinkles therein, said fluid-extending means comprising a fluid exhaust member disposed substantially intermediate opposed ends of the article for impinging the fluid flow against a surface of the edge portion to flutter the edge portion, thereby substantially smoothing-out the wrinkles, and fluid-holding means for fluidly holding the edge portion in a substantially smoothed-out state, said fluid-holding means comprising a fluid intake member disposed near an end edge of the edge portion for drawing the fluid flow generally along the surface of the edge portion, thereby holding the edge portion in said substantially smoothed-out state.

23. The assembly of claim 22 wherein said fluid exhaust member is movable toward and away from the edge portion surface, and said fluid intake member is movable along the edge portion surface.

24. The assembly of claim 23 further comprising a vortex generating means disposed with said fluid exhaust member and said fluid intake member for causing the fluid flow to turbulently impinge on the edge portion surface to flutter the edge portion.

25. The assembly of claim 22 wherein said fluid-holding means comprises a fluid duct member having an opening therein to direct a flow of fluid on the edge portion to hold it in said substantially smoothed-out state.

26. A method for handling an article having wrinkled overlapping surfaces, comprising the steps of:
receiving wrinkled overlapping surfaces,
smoothing-out the overlapping surfaces by directing a fluid flow to the wrinkled overlapping surfaces,
maintaining the surfaces in a smoothed-out condition, and discharging the smoothed-out overlapping surfaces.

27. The method of claim 26 wherein the step of directing a fluid flow includes impinging the fluid flow against the overlapping surfaces.

28. The method of claim 27 wherein the fluid flow is impinged between about 10° to about 90° relative to the overlapping surfaces.

29. The method of claim 26 wherein the step of directing a fluid flow includes drawing the fluid flow along the overlapping surfaces.

30. The method of claim 26 wherein the step of directing includes the step of generating a turbulent fluid zone near the overlapping surfaces.

31. The method of claim 30 wherein the step of generating includes moving the turbulent fluid zone relative to the overlapping surfaces.

32. The method of claim 30 wherein the step of generating includes varying the size of the turbulent fluid zone.

33. The method of claim 30 wherein the step of generating includes varying the turbulence of the turbulent fluid zone.

34. The method of claim 26 wherein the step of maintaining includes the step of delivering a fluid flow to the smoothed-out overlapping surfaces to maintain the smoothed-out condition thereof.

35. The method of claim 26 wherein the step of directing includes the step of coextending the overlapping surfaces.

36. The method of claim 26 wherein the step of smoothing-out includes off-setting the overlapping surfaces.

37. The method of claim 26 wherein the step of directing includes gently applying the fluid flow in an increasing manner to the wrinkled overlapping surfaces.

38. The method of claim 26 wherein the step of directing includes gently terminating the fluid flow in a decreasing manner to the smoothed-out overlapping surfaces.

* * * * *

UNITED STATES PATENT AND TRADEMARK OFFICE
CERTIFICATE OF CORRECTION

PATENT NO. : 5,046,272
DATED : September 10, 1991
INVENTOR(S) : Robert E. Vogt; Robert D. McQuiggin; Kenneth R. Schmidt; and Jark C. Lau It is certified that error appears in the above-identified patent and that said Letters Patent is hereby corrected as shown below:

On the Title page, item [54], and in col. 1, lines 2 and 3, delete the title "FLUID-OPERATED STABILIZING APPARATUS AND METHOD" and insert therefor --APPARATUS AND METHOD FOR FLUIDLY SMOOTHING THE WRINKLED OVERLAPPING SURFACES OF AN ARTICLE--.

Claim 14, column 8, line 39, delete the numeral "40" and insert therefor --50--.

Claim 16, column 8, line 58, add the word "fluidly" after the word "means".

Signed and Sealed this

Twelfth Day of October, 1993

Attest:

BRUCE LEHMAN

*Attesting Officer*          *Commissioner of Patents and Trademarks*